(12) United States Patent
Matusch (10) Patent No.: US 8,708,974 B2
(45) Date of Patent: Apr. 29, 2014

(54) CYLINDER-PISTON UNIT OF A DISPOSABLE INJECTOR HAVING INCREASED OPERATIONAL SAFETY

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 32 days.

(21) Appl. No.: 13/332,880

(22) Filed: Dec. 21, 2011

(65) Prior Publication Data

US 2012/0101450 A1    Apr. 26, 2012

Related U.S. Application Data

(63) Continuation-in-part of application No. PCT/EP2010/003674, filed on Jun. 17, 2010.

(30) Foreign Application Priority Data

Jun. 30, 2009   (DE) .......................... 10 2009 031 303

(51) Int. Cl.
*A61M 5/315* (2006.01)

(52) U.S. Cl.
USPC ........................................................ 604/218

(58) Field of Classification Search
USPC .......... 604/214, 217–218, 222, 258, 181, 187
See application file for complete search history.

(56) References Cited

U.S. PATENT DOCUMENTS

| 5,503,627 A | 4/1996 | McKinnon et al. |
| 2008/0287885 A1* | 11/2008 | Hoffmann et al. ............ 604/222 |

FOREIGN PATENT DOCUMENTS

| DE | 957 598 | | 2/1957 |
| EP | 1 354 609 A2 | | 10/2003 |
| WO | WO 2004/069301 A2 | | 8/2004 |
| WO | WO2007054233 | * | 5/2007 |
| WO | WO 2008/083209 A2 | | 7/2008 |
| WO | WO 2009/111794 A1 | | 9/2009 |

* cited by examiner

*Primary Examiner* — Bhisma Mehta
*Assistant Examiner* — Niyati D Shah
(74) *Attorney, Agent, or Firm* — R. S. Lombard; K. Bach (57) ABSTRACT

The end face of a cylinder-piston unit has a press-in area, engaging around the mouth, and a press-on area, surrounding the press-in area. The press-in area comprises an inner web, delimiting the mouth, and an outer web. The webs delimit a recess, which surrounds the inner web and of which the depth measured parallel to the center axis of the cylinder-piston unit is at least a quarter of its width in a plane oriented normal thereto. The press-on area, at least during an injection, is offset counter to the injection direction relative to the end face of the press-in area. Moreover, the surface of the press-on area projected into a plane normal to the center axis is at least as large as the surface of the press-in area projected into the same plane.

19 Claims, 6 Drawing Sheets

CYLINDER-PISTON UNIT OF A DISPOSABLE INJECTOR HAVING INCREASED OPERATIONAL SAFETY

CROSS-REFERENCE TO RELATED APPLICATION

This is a continuation-in-part application of pending international application PCT/EP2010/003674 filed Jun. 17, 2010 and claiming the priority of German Application No. 10 2009 031 303.6 filed Jun. 30, 2009.

BACKGROUND OF THE INVENTION

The invention relates to a cylinder-piston unit of a disposable injector, having at least one passage connecting the cylinder interior to an end-face mouth.

A cylinder-piston unit is known from DE 957 598 B. In order to prevent the formation of a tear instead of a penetration channel, a notched friction collar is formed against lateral slipping.

The object of the present invention is therefore to further increase the operational safety of a cylinder-piston unit of a disposable injector and to prevent what is called a "wet shot".

SUMMARY OF THE INVENTION

This object is achieved by the features of the main claim. For this purpose, the end face of the cylinder-piston unit has a press-in area, engaging around the mouth, and a press-on area, surrounding the press-in area. The press-in area comprises an inner web, delimiting the mouth, and an outer web. The webs delimit a recess, which surrounds the inner web and of which the depth measured parallel to the center axis of the cylinder-piston unit is at least a quarter of its width in a plane oriented normal thereto. The press-on area, at least during an injection, is offset counter to the injection direction relative to the end face of the press-in area. Moreover, the surface of the press-on area projected into a plane normal to the center axis is at least as large as the surface of the press-in area projected into the same plane.

BRIEF DESCRIPTION OF THE DRAWINGS

Further details of the invention are set forth in the in the following description of schematically depicted embodiments.

DETAILED DESCRIPTION OF THE PARTICULAR EMBODIMENTS

FIGS. 1 to 4 show a cylinder-piston unit 10 of an injector, for example of a disposable injector. Such cylinder-piston units 10 are inserted, for example for storing and for dispensing of active substances, into needle-free injectors or into injectors with integrated injection needle.

The cylinder-piston unit 10 comprises a cylinder 20 and a piston 50. When the cylinder-piston unit 10 is placed in an injector, the cylinder 20 and the piston 50 enclose, within a displacement space 30, a preparation 3 for subcutaneous, intradermal or intramuscular administration or a liquid support material, for example distilled water or physiological saline.

The cylinder-piston unit 10 is, for example, intended to be employed just once. It is used to administer a medicament volume of 0.1 to 2 ml (milliliters), for example. If appropriate, a medicament volume of 3 ml can also be administered.

The cylinder 20 approximates to the shape of the syringe barrel of a standard disposable syringe. For example, it has an internal diameter of 5.6 millimeters and an external diameter of 16.6 millimeters. At the front end 21, a passage 25 connects the cylinder interior 31 to the environment 1. This passage 25 comprises a nozzle-like discharge element 26 with a diameter of 0.2 millimeter, for example.

For better directional flow, the outflow funnel 35 does not taper linearly between the cylinder base 34 and the nozzle bore 26. The transition between the outflow funnel 35 and the nozzle bore 26 is continuous, for example. The nozzle bore 26, of which the diameter is between 0.1 and 0.5 millimeter for example, is two to four times as long as its diameter.

If appropriate, the cylinder 20 can have several passages 25 which, for example, are arranged on a common part-circle around the center line 15 or around a central passage 25.

In the illustrative embodiment, the cylinder 20 is pot-shaped, for example, and has a multi-layer wall 22 at least in some areas. The inner wall layer 23 which adjoins the cylinder interior 31, and which also engages around the passage 25, is made, for example, of an amorphous, transparent thermoplastic, for example of one or more copolymers based on cycloolefins and ethylenes or α-olefins (COC) and has a wall thickness of 1.5 millimeters. A sleeve-shaped outer wall layer 24 is integrally formed onto this inner wall layer 23, for example by two-component injection molding. This outer wall layer 24 is made of polycarbonate (PC), for example, and has a wall thickness of four millimeters in the illustrative embodiment.

The cylinder wall 22 can be formed as one layer, in which case it is made of COC, for example. In the one-layer or multi-layer configuration, it can also have a reinforcement, for example a wire mesh integrated in the wall 22.

On its end face directed toward the displacement space 30, the piston 50 has a circumferential, skirt-like sealing lip 52. This sealing lip 52 presses with pretensioning against the inner wall 27 of the cylinder. With the counteracting force increasing during the piston stroke, the pressing force of this sealing lip 52 on the inner wall 27 of the cylinder rises. The piston 50 is made of Teflon® a registered trademark of the E.I. DuPont DeNemous and Company Corporation of Wilimington, Del., for example, a polytetrafluoroethylene.

A piston rod 56 is secured on the piston 50. In the illustrative embodiment, this piston rod 56 has a diameter of five millimeters and is made of COC.

At its end directed away from the passage 25, the cylinder 20 has a stepped cross-sectional widening 28. A two part sterility closure 16, 18 sits in this cross-sectional widening 28. A first, U-shaped profile part 16 bears on the inner wall 27 of the cylinder and on the piston rod 56. A sealing ring 18 sits with a web 19 in the U-shaped opening 17. This web 19 presses the U-shaped profile part 16 onto said two structural parts 27, 56.

For connection to the drive, the cylinder-piston unit 10 has, for example, a thread 11, a bayonet attachment, a receiving slit, etc.

The end face 12 of the cylinder-piston unit 10 is divided into a press-in area 60 and, surrounding the latter, a press-on area 80. The press-in area 60 borders the mouth 29 of the passage 25. Its end face 61, in the illustrative embodiment, protrudes by 1.5 millimeters beyond the end face 81 of the press-on area 80 in the injection direction 2 of the cylinder-piston unit 10. This offset corresponds to seven and a half times the diameter of the mouth 29. It is also conceivable for the offset to be made smaller, for example five times the diameter of the mouth.

The press-in area 60 has an external diameter of two millimeters, for example. It has two webs 62, 63 pointing in the injection direction 2 and arranged coaxially to each other for example, cf. FIGS. 2 and 9. Both webs 62, 63 have in this direction a pointed edge 64, 65, for example. In the illustrative embodiment, these edges 64, 65 enclose an imaginary cone surface, of which the apex angle measures 175 degrees. The apex angle of the cone surface can lie between 165 degrees and 180 degrees, with the cone tip lying outside the cylinder-piston unit 10. It is also conceivable that the two web edges 64, 65 enclose a common plane. This plane then lies, for example, normal to the center axis 15 of the cylinder-piston unit 10.

Figure 2:
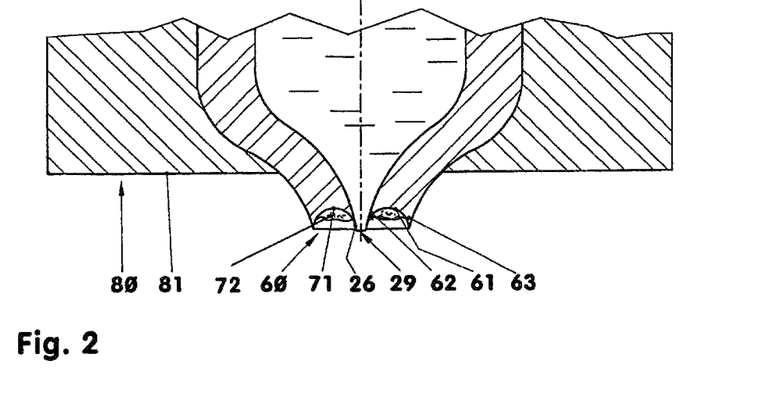
FIG. 2 shows a detail from FIG. 1.
Figure 3:
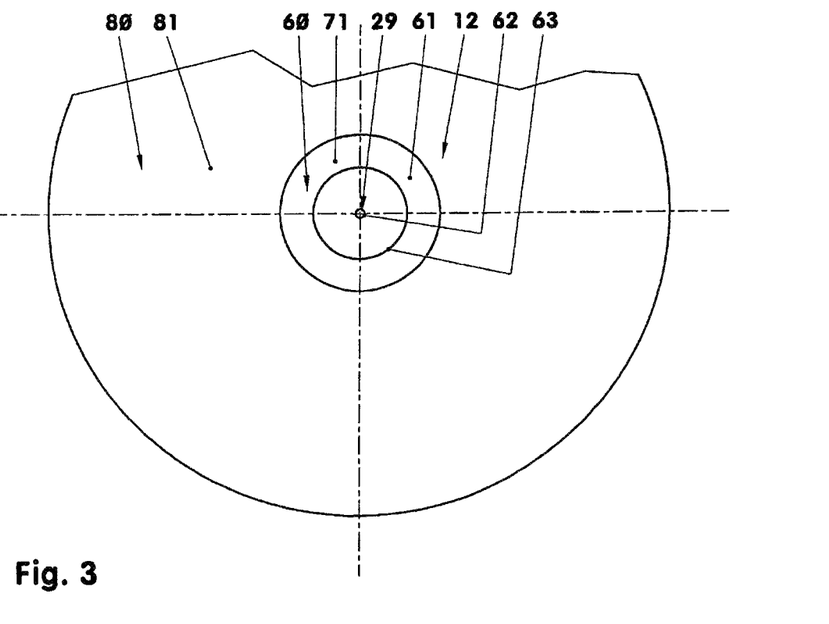
FIG. 3 shows a plan view of the end face.
Figure 9:
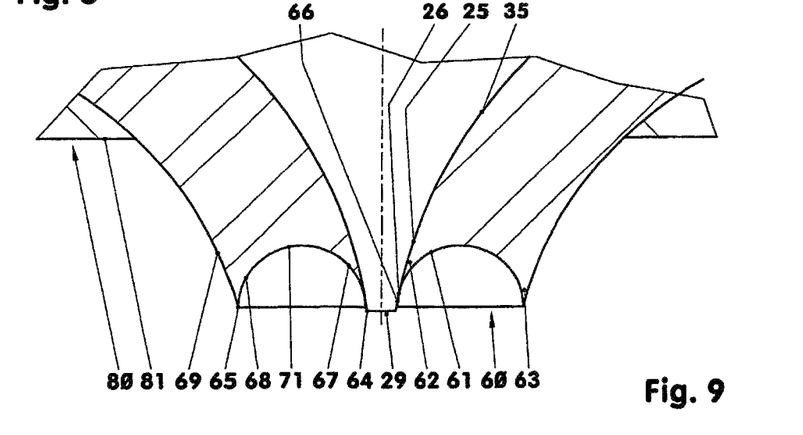
FIG. 9 shows a detail of the press-in area shown in FIG. 8.

The inner web 62 engages around the mouth 29. Its inner flank 66 forms a part of the wall of the passage 25. The concave outer flank 67 encloses an angle of 12 degrees with the inner flank 66 in the edge 64.

In the illustrative embodiment, the outer web 63 is delimited by means of two concave flanks 68, 69. The angle enclosed in the edge 65 measures 36 degrees, for example.

The angles enclosed by the web flanks 66, 67; 68, 69 in the edges 64, 65 can measure up to 45 degrees. If appropriate, the individual web 62, 63 can have, instead of the sharp edge 64, 65, an annular surface which, for example, has a width of 0.1 millimeter. In this case, the tangential planes of the web flanks 66, 67; 68, 69 adjacent to the annular surface enclose said angle. One or both web edges 64, 65 can also be designed as a half torus.

The two webs 62, 63 delimit a circumferential groove 71. In the illustrative embodiment, this recess 71 has a constant, semicircular cross section. The depth of the recess 71 measures, for example, 0.55 millimeter. For example, the cross-sectional area measures 0.48 square millimeters, that is to say, for example, 15% of the end face of the press-in area 60 projected into a plane normal to the center axis 15 of the cylinder-piston unit 10. The cross section of the recess 71 can also be semi-oval, semi-elliptic, V-shaped, rectangular, etc. An asymmetrical cross section is also conceivable.

The depth of the recess 71 measured parallel to the center axis 15 is between a quarter and three quarters of its extent in the radial direction 4 in a plane normal to the center axis 15. It can vary along the generatrix of the recess 71, which is for example the line of symmetry of the recess 71.

The press-on area 80 here comprises a flat surface 81. The latter lies in a plane normal to the center axis 15 of the cylinder-piston unit 10. This surface is, for example, 66 times as large as the end face 61 of the press-in area 60 projected onto a plane normal to the center axis 15. The ratio of the two surfaces can also be smaller. However, the end face 81 of the press-on area 80 projected into a plane normal to the center axis 15 is larger than the face 61 of the press-in area 60 projected into this plane.

Figure 1:
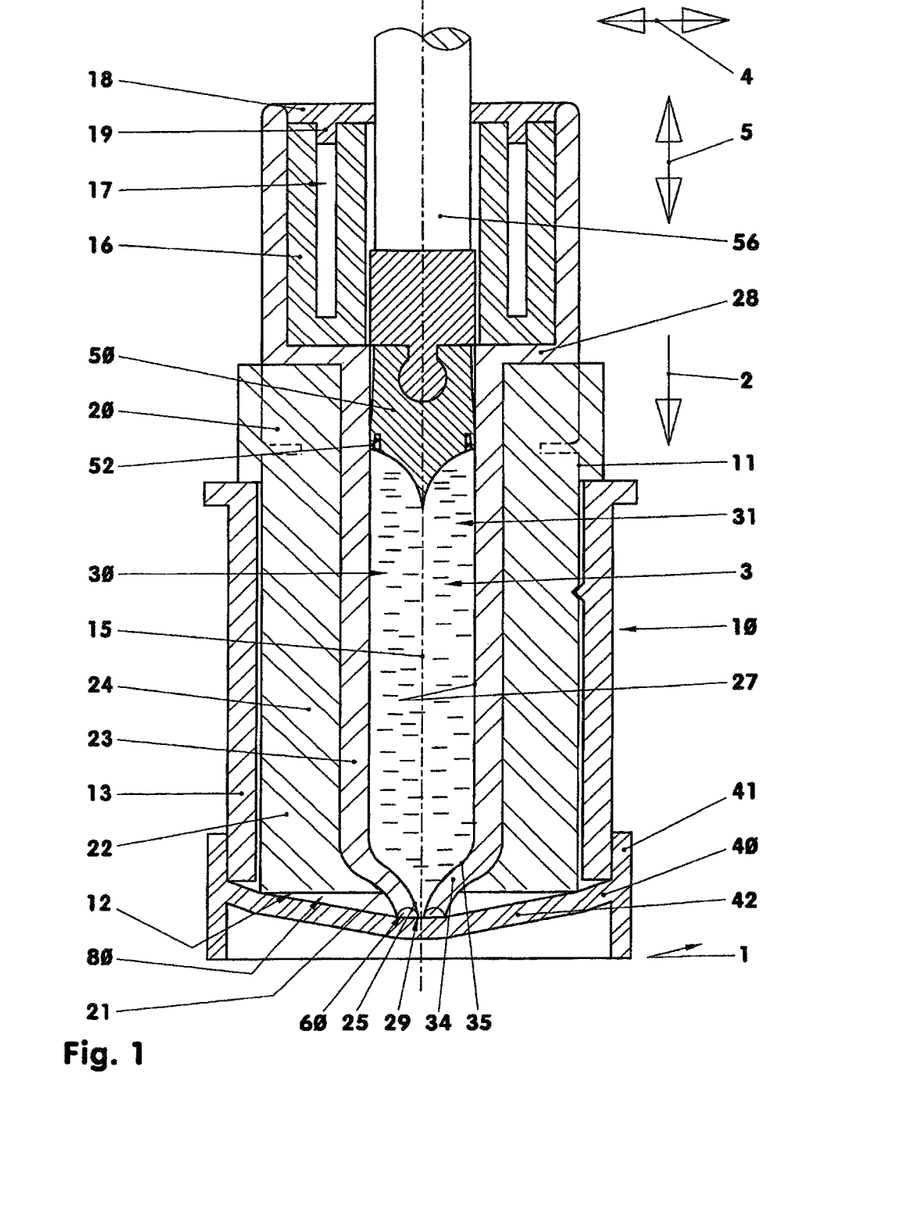
FIG. 1 shows a cylinder-piston unit with closure cap.

In FIG. 1, a sliding sleeve 13 is arranged all round the cylinder-piston unit 10. A closure cap 40 sits on this sliding sleeve 13. This closure cap 40 consists, for example, of an elastically deformable retaining ring 41 and of a membrane 42 tensioned in the latter. The membrane 42 lies elastically tensioned, for example, on the outer edge of the cylinder-piston unit 10 and on both webs 62, 63. With this three-line contact, it ensures the sterility of the press-in area 60 and of the press-on area 80. Moreover, the membrane 42 acts as a pressure relief valve, for example if air is pressed out of the chamber before the injector is used.

To use the injector, for example a disposable injector, the closure cap 40 is removed after the injection solution has been introduced and the air has been displaced from the displacement space 30. The injector is then placed with the outer end face 12 of the cylinder-piston unit 10 onto the skin 6 of the patient, cf. FIG. 4. The webs 62, 63 first touch the skin 6. They press the outer, firmer skin layer 7 in and deform it elastically. At the same time, the looser deeper skin 8 and the fatty tissue 9 lying beneath the latter are deformed. The press-on area 80 presses on the skin 6 outside the press-in area 60. In this way, the skin is held securely, such that the deformation caused by the press-in area 60 causes tensile stresses in the skin 6 that are oriented parallel to the surface.

Figure 4:
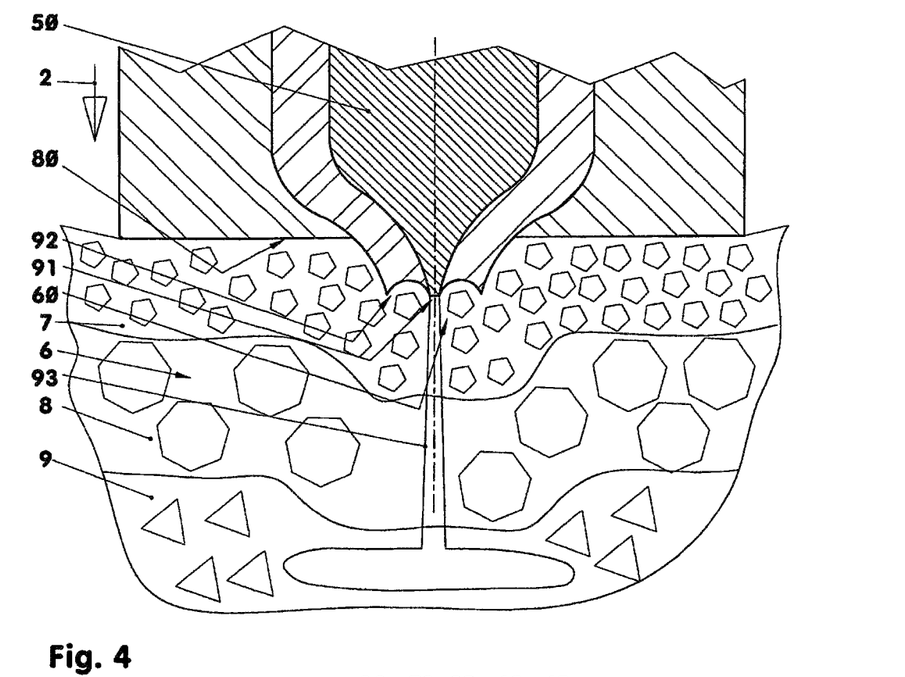
FIG. 4 shows a cylinder-piston unit placed onto the skin.

During the deformation, the skin 6 in the area 91 surrounded by the inner web 62 is stretched. The firmer skin tissue 7 is tensioned. In the area 92 enclosed by the two webs 62, 63, the skin is not pressed in. The skin engages like an O-ring, for example with a form fit, in the recess 71. In this way it seals off the area surrounded by the inner web 62, such that the injection liquid cannot escape along the skin surface. A "wet shot" is thus effectively prevented. At the same time, the loaded and unloaded areas 91, 92 of the skin 6 prevent slipping of the injector.

It is even more advantageous if the recess 71 is provided with adhesive 72, as in a sticking plaster or a transdermal therapeutic system (TTS). For this purpose, the skin 6 directly around the mouth 29 of the nozzle bore 26 is secured with high adhesive force counter to the direction of the injection jet. This means that the speed of the injection jet can be considerably reduced without danger of a "wet shot" occurring. In this way, the energy store can be reduced and every part loaded by pressure or force can have smaller dimensions.

The adhesive 72 used is, for example, a polyvinyl ether, a synthetic rubber, chlorobutadiene elastomer, etc. Multi-component adhesives can also be used. Setting takes place through partial crystallization after the evaporation of the solvent. The modulus of elasticity of the adhesive corresponds for example to the modulus of elasticity of the end face 12 of the cylinder-piston unit 10. The adhesive 72 can also be an adhesive 72 that can be used for sticking plasters, for example Collemplastrum adhaesivum DAB (German Pharmacopeia) 6. For use on greasy or sweaty skin for example, a more strongly adhering silicone adhesive can also be used.

After the injector has been triggered, the piston 50 of the cylinder-piston unit 10 is pushed forward in the direction of the mouth 29. In a subcutaneous injection, the injection liquid thereby displaced from the displacement space 30 is displaced through the firmer upper skin layer 7 and the deeper skin 8 into the subcutaneous fatty tissue 9. The tensioned, firmer skin layer 7 offers only little resistance. Therefore, the injection requires only a lower pressure than in untensioned skin. The skin channel 93 forming during the injection closes safely and thus prevents a return flow of the injection liquid. In this way, technically related underdosing of the patient can be ruled out.

Figure 5:
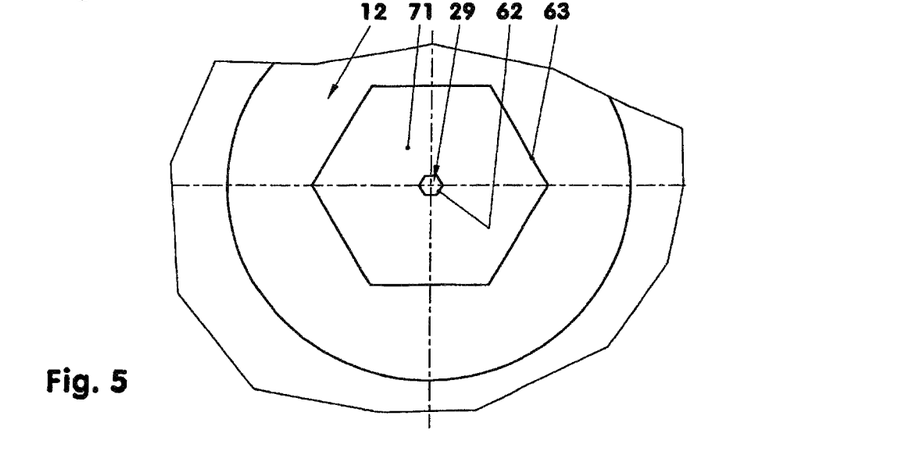
FIG. 5 shows an end face with outer web and inner web arranged in a hexagon.

FIG. 5 shows a view of the end face 12 of a cylinder-piston unit 10. The annular webs 62, 63 are arranged in the form of a hexagon, for example. In this view, the recess 71 arranged between the annular webs 62, 63 has the shape of a hexagonal ring. The cross section of the recess 71 corresponds for example to the cross section of the recess 71 shown in FIGS. 1 to 4. The webs 62, 63 can also be in the form of a triangle, square or a polygon. It is conceivable for both webs 62, 63 to be designed differently.

Figure 6:
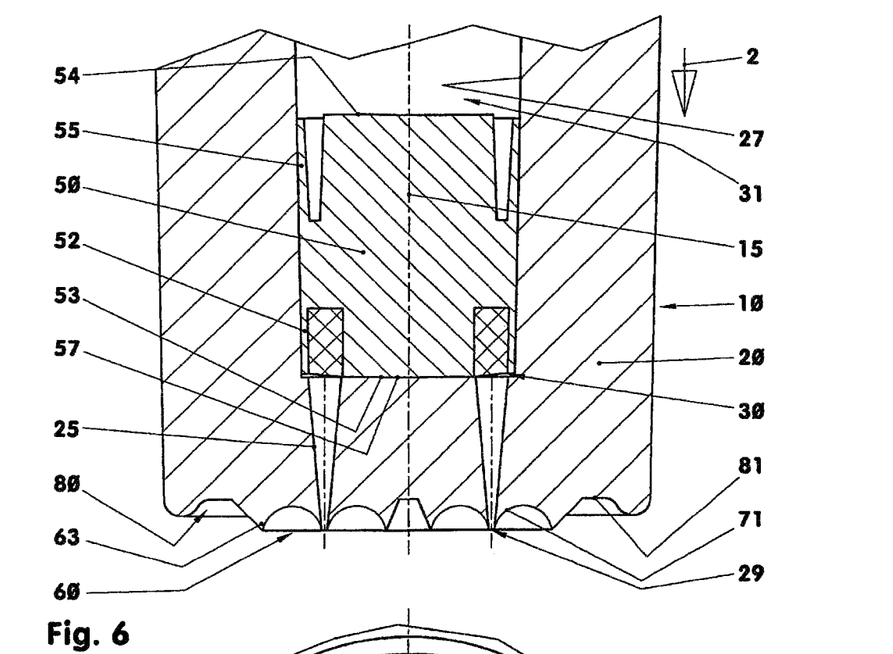
FIG. 6 shows a cylinder-piston unit with several passages.
Figure 7:
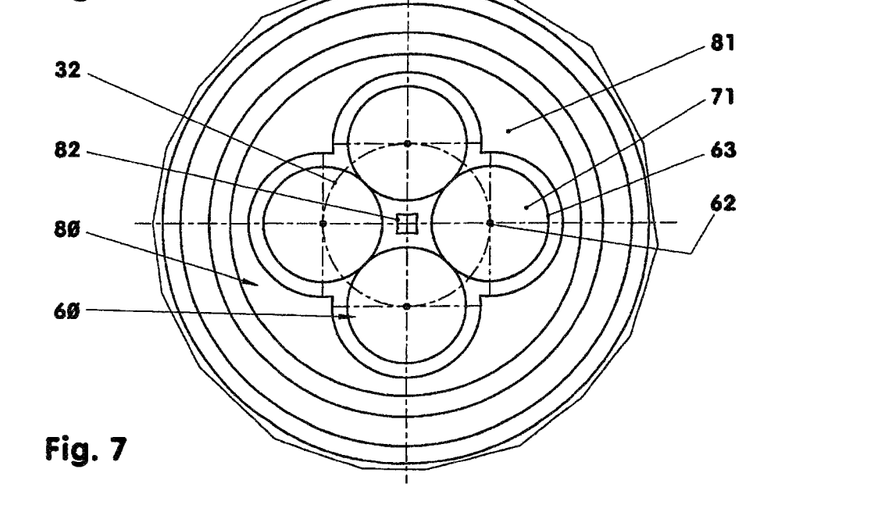
FIG. 7 shows a plan view of FIG. 6.

FIGS. 6 and 7 show another cylinder-piston unit 10 in a sectional view and in a view counter to the injection direction 2. The cylinder 20 shown in these figures is produced, for example, from a one-component material. The cylinder-piston unit 10 has, for example, four passages 25 connecting the cylinder interior 31 to the environment 1. These passages 25 lie on a common part-circle 32. In the illustrative embodiment, the cross section of all the passages 25 is identical. However, the individual passages 25 can also have different cross sections.

Each passage 25 has a mouth 29 surrounded by a press-in area 60. The individual press-in area 60 is designed as described in connection with FIGS. 1 to 4. For example, the outer webs 63 of the individual press-in areas 60 are tangent to each other. A central area 82 surrounded by all the press-in areas 60 lies in a plane with the press-on area 80 surrounding the press-in areas 60. In this illustrative embodiment, the surface 81 of the press-on area 80 arranged normal to the center axis 15 measures twice the sum of all the end faces 61 of the press-in areas 60 projected into a plane normal to the center axis 15. The projection of the end face 81 of the press-on area 80 is therefore greater than the sum of the projections of the end faces 61 of all the press-in areas 60.

At its two ends 53, 54, the piston 50 of the cylinder-piston unit 10 has protruding, pretensioned sealing cuffs 52, 55. These are pressed against the inner wall 27 of the cylinder upon movement of the piston 50. For example, the end face 57 of the piston directed toward the displacement space 30 is designed as a flat surface.

Instead of the four passages 25 shown, an embodiment with two, three, five or more passages is also conceivable. One of the passages 25 can be arranged centrally in such an embodiment.

When an injector with such a cylinder-piston unit 10 is applied, the skin of the patient is deformed in the area of each individual press-in area 60 as described in connection with the first illustrative embodiment. The skin engages in the groove-shaped recesses 71, such that the area surrounding each individual mouth 29 is sealed off.

The press-on area 80 prevents slipping of the upper skin layer 7, such that the latter is tensioned by means of the press-in area 60 for the injection. In this illustrative embodiment also, a low-pressure and safe injection is thus permitted, with the advantage that bubble formation is avoided, since the total volume is distributed among several partial volumes.

Figure 8:
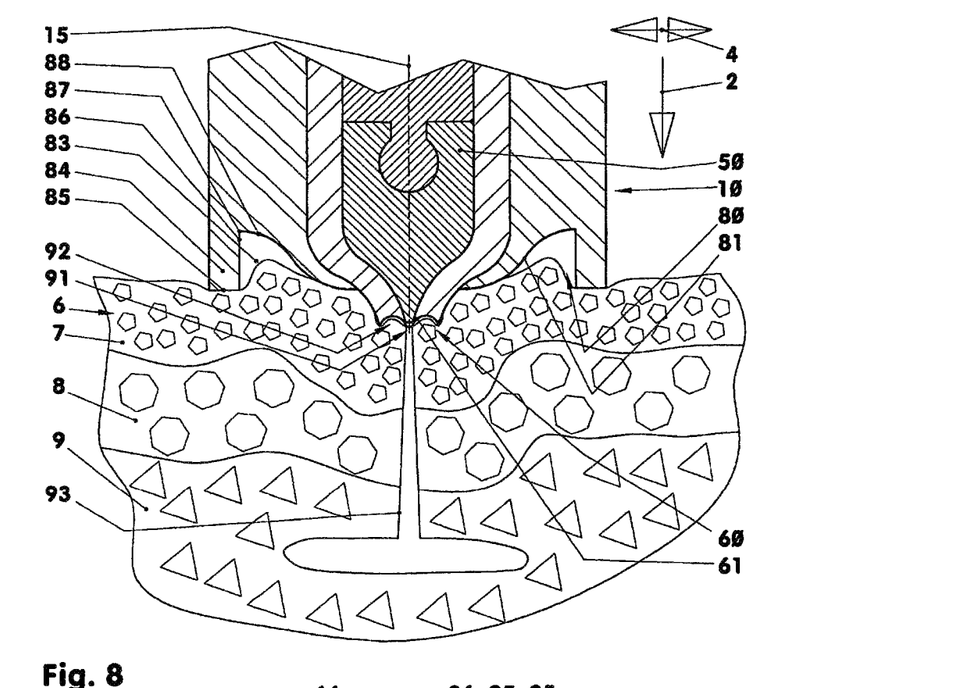
FIG. 8 shows a cylinder-piston unit with two sealing areas.

FIG. 8 shows a cylinder-piston unit 10 with main dimensions corresponding to the main dimensions of the cylinder-piston unit 10 shown in FIGS. 1 to 4. The design of the press-in area 60 also corresponds to the design described there.

The press-on area 80 has a circumferential groove 83. The latter is delimited in the radial direction 4 by means of a depressor 84. The size of the end face 85 of the depressor 84 corresponds to ten times the end face 61 of the press-in area 60 projected onto a plane normal to the center axis 15 of the cylinder-piston unit 10.

The flank 86 of the for example approximately V-shaped groove 83, which flank 86 is adjacent to the depressor 84, is for example oriented normal to the end face 85 of the depressor 84. In the illustrative embodiment, the depth of the groove 83 corresponds to the diameter of the press-in area 60.

The inner flank 88 adjacent to the groove base 87 is concave and merges into a convexly curved surface in the direction of the end face 81.

When the cylinder-piston unit 10 is placed onto the skin 6, the latter, as has been described in connection with the first illustrative embodiment, is tensioned in the portion 91 loaded by the press-in area 60. In the press-on area 80 offset counter to the injection direction 2, the depressor 84 prevents the skin from slipping. In the area of the groove 83, the skin 6 nestles against the contour of the groove 83 and thus forms a second seal, for example a form-fit seal, of the area delimited by the inner web 62, such that the injection liquid is forced into the skin channel 93. At the same time, the less loaded skin 6 in the area of the groove 83 prevents slipping of the injector.

During the injection, the injection liquid can therefore pass safely into the subcutaneous fatty tissue 9.

Figure 10:
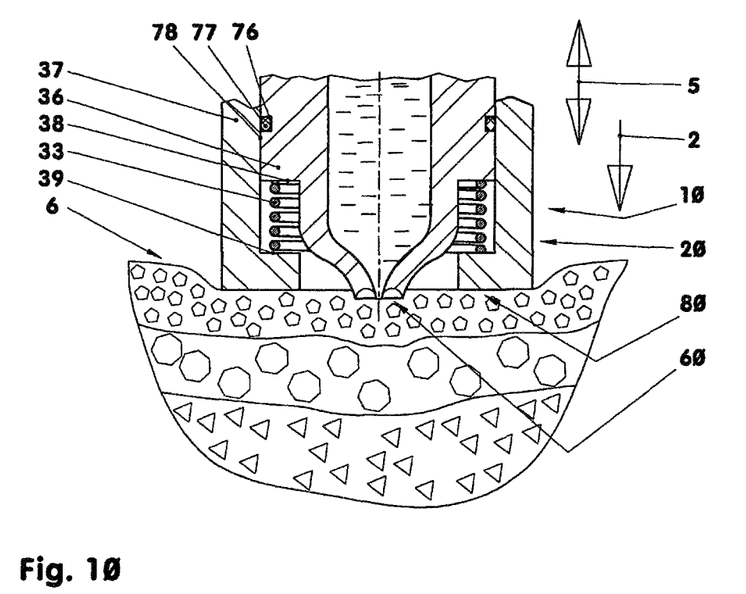
FIG. 10 shows a cylinder-piston unit with a press-in area and a press-on area that are axially movable relative to each other.
Figure 11:
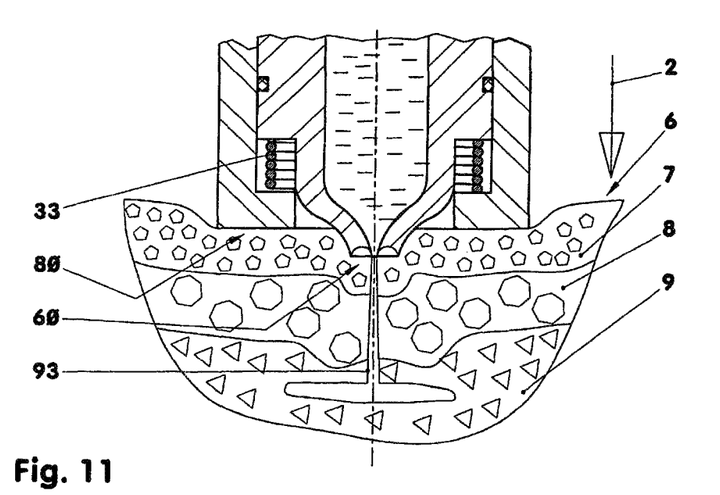
FIG. 11 shows a cylinder/piston unit of FIG. 10 during an injection.

FIGS. 10 and 11 show another cylinder-piston unit 10. The cylinder 20 is designed in two parts and has an inner part 36 and, coaxial thereto, an outer part 37. The inner part 36 is movable relative to the outer part 37 in an axial direction 5. A spring 33, for example a compression spring, is arranged between a support surface 38 of the inner part 36 and a bearing surface 39 of the outer cylinder part 37. An O-ring 77 fitted in an annular groove 76 of the inner cylinder 36 prevents entry of germs through the gap 78 between the inner cylinder 36 and outer cylinder 37 and thus seals off the press-on area 80 in a sterile manner.

FIG. 10 shows the cylinder-piston unit 10 when placed onto the skin of the patient. The press-on area 80 of the outer cylinder 37 bears on the skin 6. The press-in area 60 of the inner cylinder 36 is pressed slightly into the skin 6. In this view, it is offset, for example by 0.5 millimeter, in relation to the press-on area 80 in the injection direction 2. However, the press-in area 60 can also be offset in relation to the press-on area 80 counter to the injection direction 2 before the injection. The compression spring 33 is unloaded. A triggering of the injector, for example, is not possible in this state.

When the injector is pressed on further, the inner cylinder 36 is moved relative to the outer cylinder 37 in the injection direction 2, cf. FIG. 11. The spring 33 is compressed. In this way, the pressure on the press-on area 80 is increased. At the same time, the press-in area 60 tensions the skin 6 as the stroke increases. In the view in FIG. 11, the press-in area 60 is offset relative to the press-on area 80 in the injection direction 2 by 1.5 millimeter, for example. The injection is now released and triggered. Forming a skin channel 93 through the skin layers 7, 8, the injection liquid shoots into the fatty tissue 9.

Combinations of the described illustrative embodiments are also conceivable.

LIST OF REFERENCE SIGNS

1 environment
2 injection direction
3 preparation
4 radial direction
5 axial direction
6 skin
7 firm upper skin
8 deeper skin
9 fatty tissue
10 cylinder-piston unit
11 thread
12 end face of (10)

13 sliding sleeve
15 enter line, center axis
16 U-shaped profile part, sterility closure
17 opening of (17)
18 sealing ring
19 web
20 cylinder
21 front end
22 cylinder wall
23 inner wall layer
24 outer wall layer
25 passage
26 discharge element, nozzle bore
27 inner wall of cylinder
28 cross-sectional widening
29 mouth
30 displacement space
31 cylinder interior
32 part-circle
33 spring, compression spring
34 cylinder base
35 outflow funnel
36 inner part, inner cylinder
37 outer part, outer cylinder
38 support surface
39 bearing surface
40 closure cap
41 retaining ring
42 membrane
50 piston
52 sealing lip, sealing cuff
53 end of (50)
54 end of (50)
55 sealing cuff
56 piston rod
57 end face of piston
60 press-in area
61 end face
62 inner web
63 outer web
64 edge
65 edge
66 inner flank
67 outer flank
68 inner flank
69 outer flank
71 recess, groove
72 adhesive
76 annular groove
77 sealing ring, O-ring
78 gap
80 press-on area
81 end face
82 central area
83 groove, recess
84 depressor
85 end face of (84)
86 flank
87 groove base
88 inner flank
91 area of (6)
92 area of (6)
93 skin channel

What is claimed is:

1. A cylinder-piston unit (10) of a needle-free disposable injector, comprising:
a cylinder (20) and an end face (12) including at least one nozzle-like discharge element (26) each having a mouth (29), the cylinder (20) having a cylinder interior (31) having at least one passage (25), each of said passage (25) connecting the cylinder interior (31) to one of said at least one mouth (29),
the first end face (12) of the cylinder-piston unit (10) has at least one skin press-in area (60), each engaging around one of said at least one mouth (29), and a skin press-on area (80), surrounding the at least one skin press-in area (60), the skin press-on area (80) having a first surface (81),
each of the at least one skin press-in area (60) comprises an inner circumferential web (62), delimiting one of said at least one nozzle-like discharge element (26) having the mouth (29) protruding beyond the first surface (81) of the skin press-on area (80), and an outer circumferential web (63) in surrounding relationship with the inner circumferential web (62), each of the webs (62, 63) for pressing into skin (6) in an operative position of the injector, the inner circumferential web (62) in the operative position of the injector is configured for stretching the skin (6) in an area (91) surrounded by said inner circumferential web (62),
the inner circumferential web (62) and the surrounding outer circumferential web (63) each protrude beyond the first surface (81) of the skin press-on area (80) and delimit a first recess (71) between the inner circumferential web (62) and the surrounding outer circumferential web (63) for receiving and forming an O-ring shaped skin (6) area (92) for sealing off and preventing wet shots of one of said at least one nozzle-like discharge element (26), the O-ring shaped skin (6) area (92) surrounds the inner circumferential web (62) and of which a depth of the O-ring shaped skin area (92) measured parallel to a center axis (15) of the cylinder-piston unit (10) is at least a quarter of its width in a plane oriented normal thereto,
the skin press-on area (80), at least during an injection, is offset counter to an injection direction (2) relative to an end face segment (61) of one of the at least one press-in skin area (60),
the first surface (81) of the press-on skin area (80) projected into a plane normal to the center axis (15) is at least as large as a second surface of the end face segment (61) of the at least one press-in skin area (60) projected into the same plane,
an adhesive (72) is operatively positioned on the first recess (71), and,
the press-on skin area (80) has a second recess (83) for receiving skin (6) for forming a second seal and preventing wet shots of said at least one nozzle-like discharge element (26).

2. The cylinder-piston unit (10) as claimed in claim 1, wherein the webs (62, 63) have edges (64, 65), which lie in one plane or enclose a conical surface having an apex angle lying between 165 degrees and 180 degrees.

3. The cylinder-piston unit (10) as claimed in claim 1, wherein a cross section of the first recess (71) is constant along its generatrix.

4. The cylinder-piston unit (10) as claimed in claim 1, wherein the cylinder (20) includes a depressor (84) for contacting the skin (6) and delimiting the second recess (83), the second recess (83) is coaxial to the center axis (15) of the cylinder-piston unit (10).

5. The cylinder-piston unit (10) as claimed in claim 4, wherein the depressor (84) is surrounding relationship with respect to the second recess (83) and is for delimiting the second recess (83) in a radial direction with respect to the center axis (15).

6. The cylinder-piston unit (10) as claimed in claim 5, wherein the depressor (84) is configured in the operative position of the injector for preventing a slippage of skin (6) in an area of the second recess (83).

7. The cylinder-piston unit (10) as claimed in claim 1, wherein the cylinder (20) comprises two passages (25) operatively arranged on a common-part circle around the axis (15).

8. The cylinder-piston unit (10) as claimed in claim 1, wherein the cylinder (20) of the cylinder-piston unit (10) comprises an inner cylinder (36) and, surrounding the latter, an outer cylinder (37).

9. The cylinder-piston unit (10) as claimed in claim 8, wherein the inner cylinder (36) includes a support surface (38) and the outer cylinder (37) includes a bearing surface (39), a spring (33) is operatively positioned between the support surface (38) and the bearing surface (39), the inner cylinder (36) is movable relative to the outer cylinder (37) in the injection direction (2) under a load exerted by the spring (33).

10. The cylinder-piston unit (10) as claimed in claim 1, wherein the end face segment (61) protrudes a predetermined distance beyond the first surface (81) of the press-on area (80).

11. The cylinder-piston unit (10) as claimed in claim 1, wherein the webs (62, 63) are arranged coaxially with respect to each other and include pointed edges (64, 65).

12. The cylinder-piston unit (10) as claimed in claim 11, wherein inner circumferential web (62) includes an inner flank (66) proximate the edge (64) in engagement relationship around the one of the said at least one mouth (29).

13. The cylinder-piston unit (10) as claimed in claim 12, wherein the inner circumferential web (62) further includes a concave outer flank (67).

14. The cylinder-piston unit (10) as claimed in claim 13, wherein the concave outer flank (67) encloses an angle from about 12 degrees to about 45 degrees with respect to the inner flank (66).

15. The cylinder-piston unit (10) as claimed in claim 11, wherein the outer web (63) is delimited by two concave flanks (68, 69) proximate the edge (65).

16. The cylinder-piston unit (10) as claimed in claim 15, wherein the two concave flanks (68, 69) of the edge (65) enclose an angle from about 36 degree to about 45 degrees.

17. The cylinder-piston unit (10) as claimed in claim 11, wherein the at least one of edge (64, 65) is formed as a half torus.

18. The cylinder-piston unit (10) as claimed in claim 1, wherein the first recess (71) is circumferential and has a constant, semi-circular cross-section or semi-oval cross-section or semi-elliptic cross-section or V-shaped cross-section or rectangular cross-section.

19. The cylinder-piston unit (10) as claimed in claim 1, wherein the first recess (71) is formed as a hexagonal ring or a triangular ring or a square ring.

\* \* \* \* \*